(12) United States Patent
Gonzalez de la Rosa

(10) Patent No.: US 9,808,149 B2
(45) Date of Patent: Nov. 7, 2017

(54) ANALYSIS METHOD

(71) Applicant: Oculus Optikgeraete GmbH, Wetzlar (DE)

(72) Inventor: Manuel Gonzalez de la Rosa, Santa Cruz de Tenerife (ES)

(73) Assignee: OCULUS OPTIKGERAETE GMBH, Wetzlar (DE)

( * ) Notice: Subject to any disclaimer, the term of this patent is extended or adjusted under 35 U.S.C. 154(b) by 170 days.

(21) Appl. No.: 14/313,337

(22) Filed: Jun. 24, 2014

(65) Prior Publication Data

US 2014/0375955 A1    Dec. 25, 2014

(30) Foreign Application Priority Data

Jun. 25, 2013  (EP) .................................... 13173632

(51) Int. Cl.
*A61B 3/00* (2006.01)
*A61B 3/024* (2006.01)
(Continued)

(52) U.S. Cl.
CPC ............ *A61B 3/0025* (2013.01); *A61B 3/024* (2013.01); *A61B 3/102* (2013.01); *A61B 3/12* (2013.01);
(Continued)

(58) Field of Classification Search
CPC ......... A61B 3/0025; A61B 3/024; A61B 3/10; A61B 3/1005; A61B 3/1233; A61B 3/102
(Continued)

(56) References Cited

U.S. PATENT DOCUMENTS

| | | | |
|---|---|---|---|
| 5,868,134 A | 2/1999 | Sugiyama et al. | |
| 2004/0066489 A1* | 4/2004 | Benedikt | A61B 3/107 351/212 |

(Continued)

FOREIGN PATENT DOCUMENTS

| | | |
|---|---|---|
| EP | 2361547 A1 | 8/2011 |
| EP | 2449957 A1 | 5/2012 |

(Continued)

OTHER PUBLICATIONS

R.S. Harwerth et al: "Linking structure and function in glaucoma", Progress in Retinal and Eye Research, vol. 29, No. 4, Jul. 1, 2010 (Jul. 1, 2010), pp. 249-271, XP055080974, 10.1016—J.Perteyers. 2010.02.001 ISSN: 1350-9462.

(Continued)

*Primary Examiner* — Darryl J Collins
*Assistant Examiner* — Journey Sumlar
(74) *Attorney, Agent, or Firm* — King & Schickli, PLLC

(57) ABSTRACT

An analysis method for determining a morphological property of an optic disc and/or a retinal nerve fiber layer of an eye is, performed an ophthalmological device, in particular a perimeter, and also means for data processing using a database with functional data of a field of vision and morphological data of the optic disc and/or retinal nerve fiber layer, wherein, by the ophthalmological device, functional data of a field of vision of the eye are measured, a retina being divided into points representing the field of vision, optical stimuli of a defined intensity being provided to the points of the retina, a reaction to a stimulus being determined as a measuring result of a point, the measuring results having a statistically significant relation to morphological data of the optic disc and/or the retinal nerve fiber layer, the morphological data nerve fiber layer being derived from the measuring results and the datasets.

17 Claims, 8 Drawing Sheets

(51) Int. Cl.
A61B 3/10 (2006.01)
A61B 3/12 (2006.01)
G06T 7/00 (2017.01)
G06T 7/62 (2017.01)

(52) U.S. Cl.
CPC .............. *G06T 7/0012* (2013.01); *G06T 7/62* (2017.01); *G06T 2207/10101* (2013.01); *G06T 2207/20076* (2013.01); *G06T 2207/30041* (2013.01)

(58) Field of Classification Search
USPC ........................... 702/19; 351/224–226, 246
See application file for complete search history.

(56) References Cited

U.S. PATENT DOCUMENTS

2009/0073387 A1    3/2009    Meyer et al.
2013/0148081 A1    6/2013    Tanaka et al.

FOREIGN PATENT DOCUMENTS

JP    2012100713 A    5/2012
JP    2013501553 A    1/2013

OTHER PUBLICATIONS

Renato Lisboa et al: "Combining structure and function to evaluate glaucomatous progression: implications for the design of clinical trials", Current Opinion in Pharmacology, vol. 13, No. 1, pp. 115-122, XP055080976, Issn; 1471-4892 Feb. 1, 2013 (Feb. 1, 2013).

Nicholas G Strouthidis et al: "Structure and Function in Glaucoma: The Relationship between a Functional Visual Field Map and an Anatomic Retinal Map", Investigative Ophthalmology & Visual Science—IOVS, Association for Research in Vision and Ophthalmology, US, vol. 47, No. 12, Dec. 1, 2006 (2006 Dec. 1, 2006), pp. 5356-5362, XP 887922457, ISSN; 8146-8448.

* cited by examiner

Fig. 1
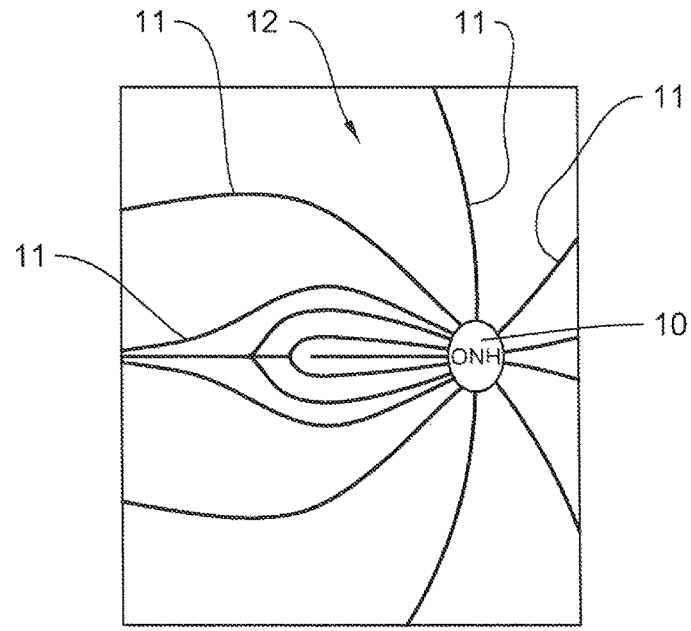
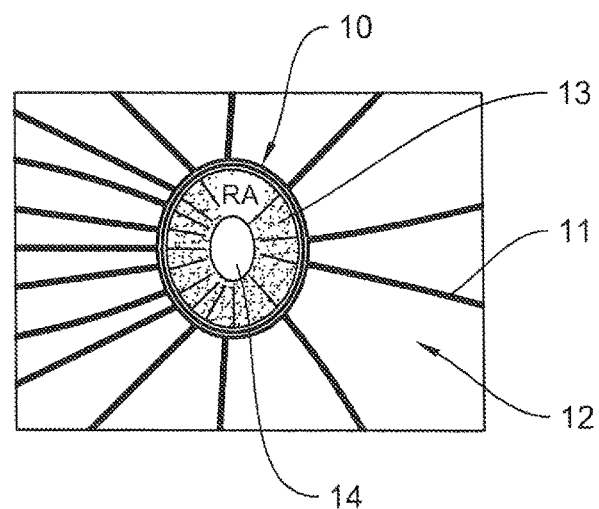
Fig. 2

Fig. 3
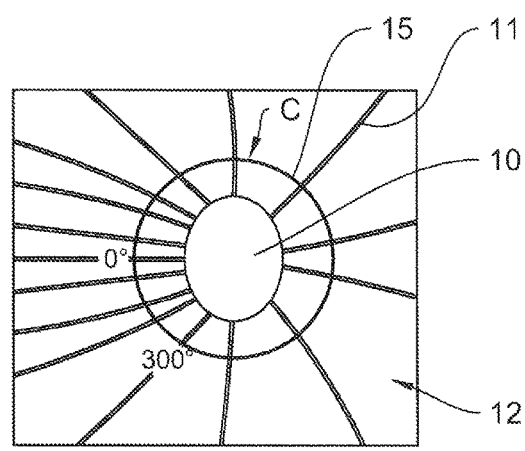
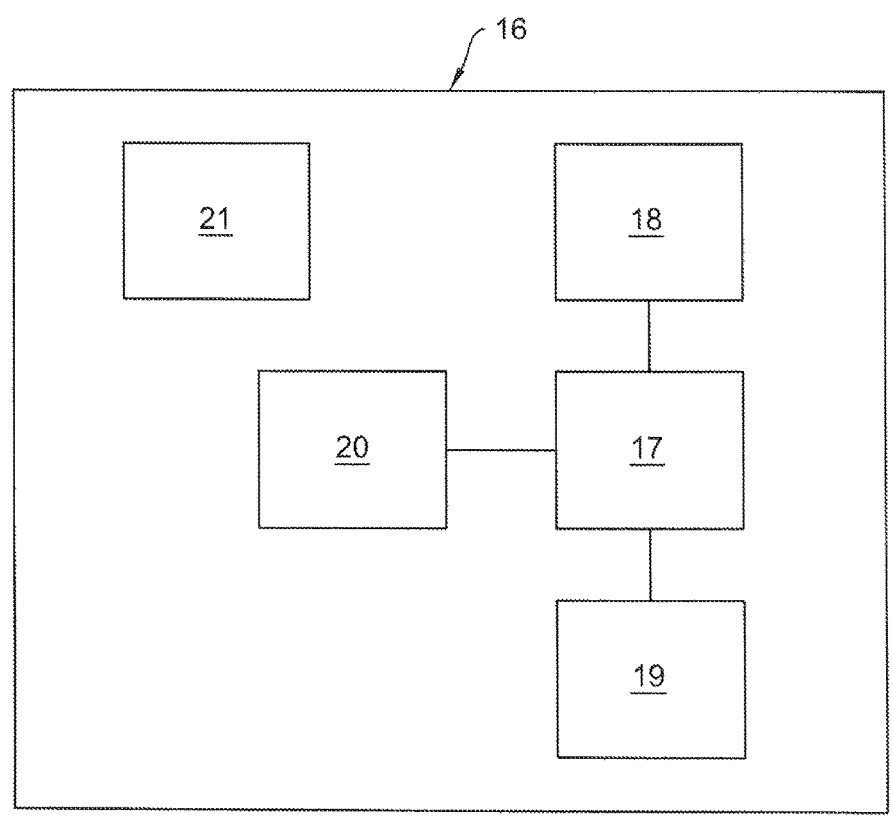
Fig. 4

Fig. 8
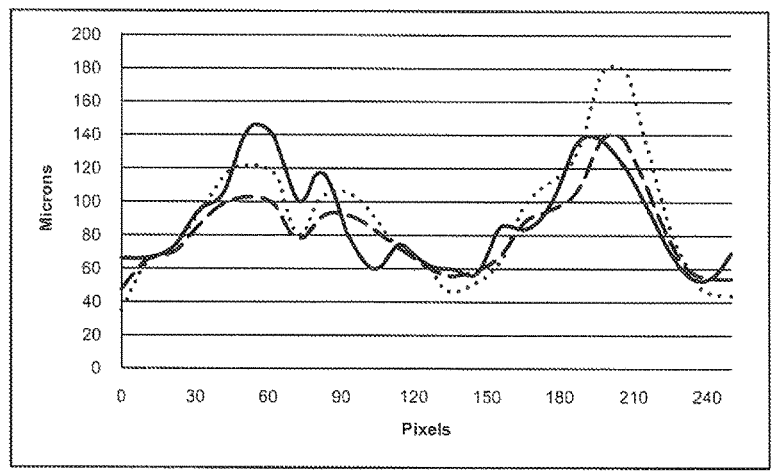
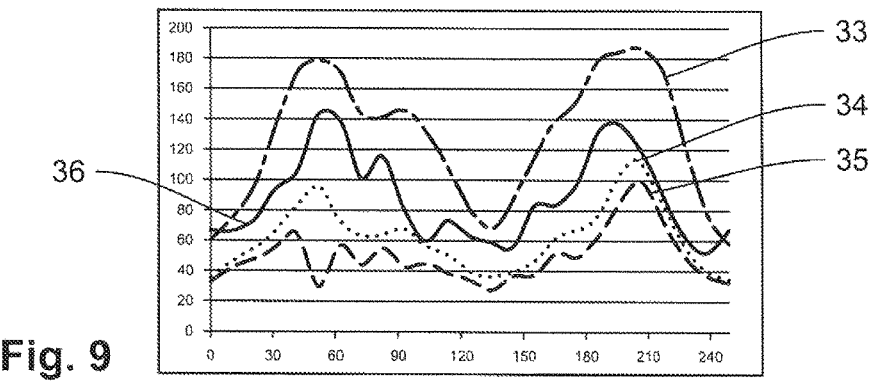
Fig. 9
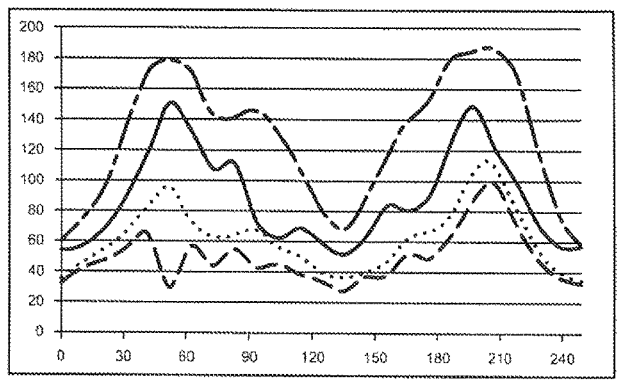
Fig. 10

Fig. 14
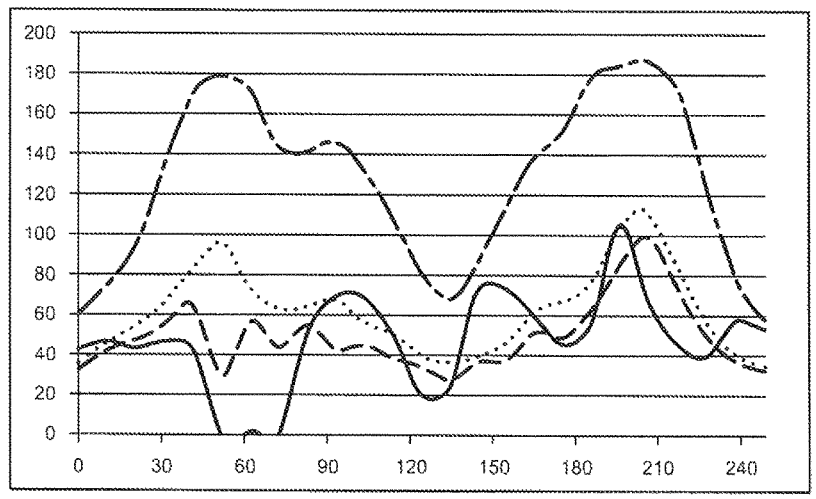
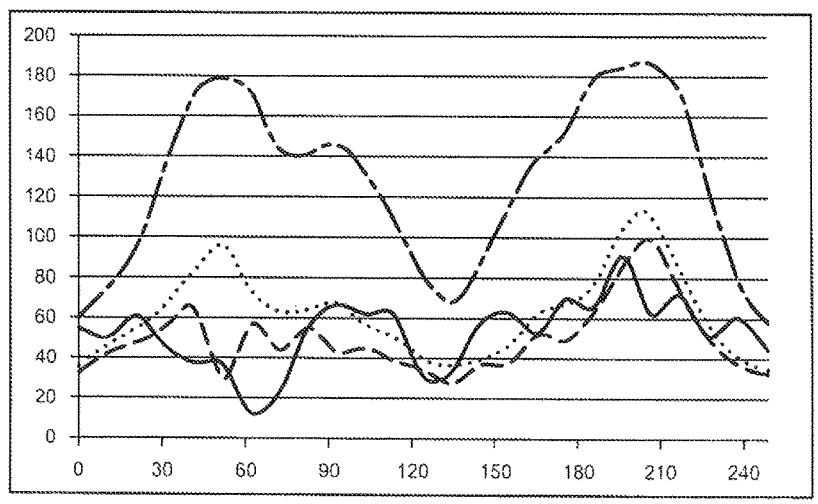
Fig. 15

Fig. 16
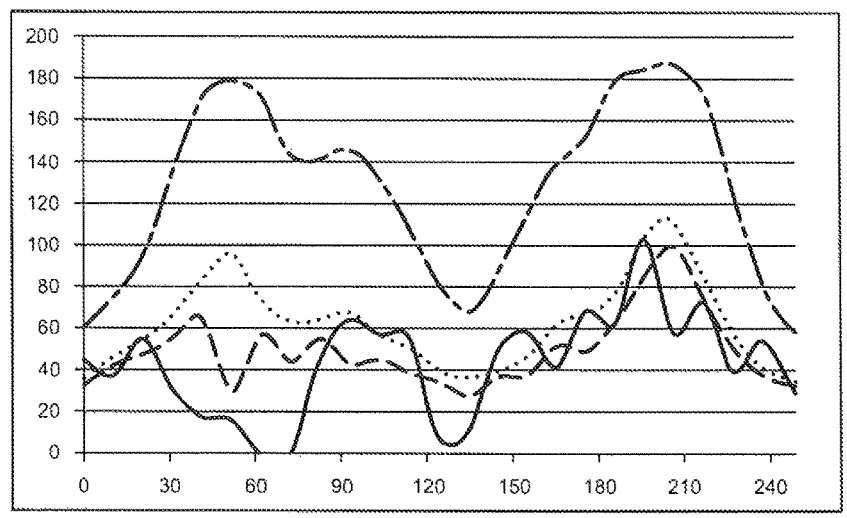
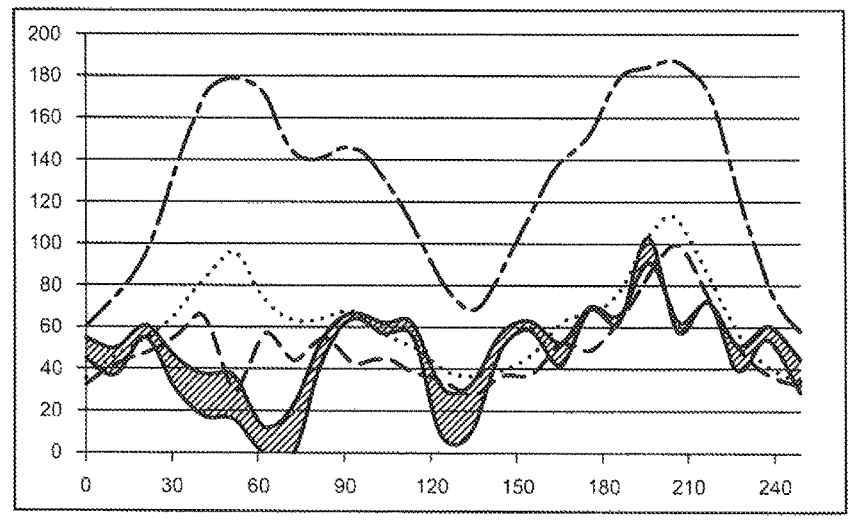
Fig. 17

ANALYSIS METHOD

The disclosure of European Patent Application No. 13173632.4, filed Jun. 25, 2013, is incorporated herein by reference.

TECHNICAL FIELD

The invention relates to an analysis method for determining a morphological property of an optic disc and/or a retinal nerve fiber layer of an eye having the features of claim 1, and also to an ophthalmological device configured for the implementation of the method.

BACKGROUND

A measurement or determination of a morphological property of an optic disc and/or a retinal nerve fiber layer of an eye serves inter alia the purpose of recognizing glaucoma. Glaucoma always leads to a loss of nerve fibers in the area of the optic disc or in the area of an exit site of an optic nerve, respectively. This manifests in a progressive excavation of the optic disc, which is also called optic nerve head. As a result of the loss of nerve fibers, degenerations of the field of vision, or so-called scotoma, occur. Thus, glaucoma leads to morphological defects because of damage to nerve pathways and to functional defects in the form of scotoma.

Scotoma can be determined by an examination of the field of vision or by perimetric measurements, respectively. In a perimetric examination of a field of vision of an eye, a patient is exposed to optical stimuli, the patient giving feedback as to whether he recognized a stimulus or not. For instance, perimeters are known in which a patient looks into a hemisphere or a flat screen, via which, controlled by a computer, spots of light are projected in different positions and at various levels of brightness. In this way, it is possible to examine both the overall extent of a visual field and the condition of selected regions thereof. A brightness of the points of light may be varied in such manner that a threshold value above which the patient detects the point of light can be determined for a position on the retina.

Various methods for determining visual fields and threshold values are known from the state of the art. In essence, a series of stimuli with various gradations of brightness are directed at a point on the retina to be measured or tested, so that the specific threshold value for the point may be determined. In order to localize a threshold value, this may be carried out with uniform or non-uniform gradations of stimuli, for example. Additionally, a database containing representative threshold values of an individual person may be incorporated. For example, a possible threshold value may be localized within a threshold range taking into account a patient's age and sex. It is also known that there is a relationship between directly adjacent regions or measured points in the retina. For instance, threshold values typically do not differ substantially between neighboring points. Accordingly, a threshold value for a directly adjacent point may be sought within a probable threshold value range. It is an objective of the known perimetric methods to determine a field of vision as precisely as possible with a number of stimuli as low as possible being provided to a patient. From EP 2 361 547 A1, for example, a perimetry method is known in which a complete measurement of the field of vision can be carried out with the help of a very low number of stimuli or measured points of an eye's retina. Also, a series of other, different perimetric methods are known by means of which a determination of a field of vision is possible. However, all the aforementioned methods only provide a determination of functional data of a field of vision because it is a subjective measurement of a recognition of stimuli by the patient.

Morphological defects in the area of the retinal nerve fiber layer, optic disc or optic nerve head can be determined and measured by means of imaging methods, such as Confocal Heidelberg Retinal Tomography (HRT), Scanning Laser Polarimetry (GDx) and Optical Coherence Tomography (OCT). For example, an OCT measurement allows a depth measurement of the retina and also measuring, in the area near to the optic nerve head or optic disc, a thickness of a sheet or layer of optic nerves leaving the optic nerve head. In the course of this, inter alia, a reduction of a neuroretinal ring can be measured as well.

Primarily, it is desirable to be able to recognize the development of glaucoma at an early stage. While morphological and functional defects can occur simultaneously, it is also possible that morphological defects are recognizable before any functional effects occur. Nevertheless, functional defects always have the underlying cause of morphological defects. The functional consequences of morphological defects, however, are individually different so that a direct link cannot always be established. For instance, a measured nerve fiber layer thickness in a person can be without functional effects and thus lie in a normal range, whereas the same nerve fiber layer thickness in another person does already lead to functional degenerations. The nerve fibers form a compact mass, thus morphological damage to one area cannot be associated to only one area of the field of vision. Also, such a morphological defect can have an impact on multiple areas of the field of vision. Even in a more detailed analysis of an area of the field of vision it is unknown which of the analyzed points have a more or less close connection to the morphological damage. Hence, only imprecise conclusions concerning scotomas can be drawn from an objective measurement of an optic disc by means of an imaging method since scotomas are subject to individual variations. Conversely, while there are always morphological defects when there are functional defects, it is excluded for the afore-mentioned reasons that a statement concerning morphological defects is possible at all with sufficient accuracy on the basis of functional defects.

Nevertheless, the afore-mentioned imaging methods for measuring an optic disc are especially useful for the early diagnosis of glaucoma because they can detect even minimal damage to the optic disc. It is, however, a disadvantage of the imaging methods that the respective ophthalmological devices are much more expensive than the devices used for perimetric methods. An OCT measurement of an optic disc is thus much costlier than a perimetric measurement of a field of vision.

Therefore, it is the task of the present invention to propose a method and an ophthalmological device which allows a determination of morphological defects in the area of the optic disc with sufficient accuracy.

SUMMARY

This task is solved by an analysis method having the features of claim 1 and by an ophthalmological device having the features of claim 16.

The analysis method for determining a morphological property of an optic disc and/or a retinal nerve fiber layer of an eye is performed by means of an ophthalmological device, in particular a perimeter or the like, and also means for data processing comprising a database, the database comprising datasets with functional data of a field of vision and morphological data of an optic disc and/or a retinal nerve fiber layer, wherein, by means of the ophthalmological device, functional data of a field of vision of the eye are measured, a retina of the eye being divided into points, which represent the field of vision, optical stimuli of a defined intensity being provided to the points of the retina, a reaction to a stimulus being determined as a measuring result of a point, the measuring results of the points having a statistically significant relation to morphological data of an optic disc and/or a retinal nerve fiber layer of the eye, the morphological data of the optic disc and/or the retinal nerve fiber layer of the eye being derived from the measuring results of the points and from the datasets.

In this way it becomes possible to make a statement concerning potentially present morphological damage to an optic disc with the help of an extended perimetric analysis method and/or with a comparably inexpensive ophthalmological device. The analysis method thus allows an improved early recognition of glaucoma. In particular due to the fact that, between the points of the retina and the measuring results of said points, there is a statistical connection to areas of the optic disc and to the morphological measuring results of the areas, it is possible to store this statistical relation in the database and use it to obtaining further measuring results. When perimetrically measuring an eye, the measuring results of the measured points are then processed with the help of the means for data processing, preferably a computer, under consideration of the statistical relation so that the morphological data of the eye's optic disc can be derived. Thus, there is no direct measurement of the morphological data taking place, but the derivation of the morphological data from the measurement of the field of vision and from the functional data of the field of vision. The obtained morphological data of the optic disc thus are based on the subjective perimetric determination of the functional data of the field of vision; yet they are approximated with high accuracy to the factual morphological data of the optic disc that are not being measured here. In this manner, a qualified statement within the course of an early diagnosis of glaucoma can be made owing to the thus derived morphological data of the optic disc without an imaging measurement method needing to be employed. If signs of beginning deterioration of the optic disc are suggested by the perimetric measurement, an objective measurement with an imaging method can be performed subsequently to obtain morphological measuring results. Basically, it is not even necessary that the derivation of the morphological data has a direct relation in time to the collection of the perimetric data.

It is particularly advantageous if the database comprises a multitude of datasets to be associated with eyes, wherein each dataset can comprise functional datasets of a field of vision and morphological data of an optic disc. The datasets can for example be acquired in that a number of eyes of different subjects are measured, functional data is determined for each eye by means of a perimetric measurement and morphological data is determined for each eye by means of an imaging measuring method, such as an OCT measurement. Since it is not possible to determine functional data in the area of the optic disc or optic nerve head only by a perimetric measurement due to the blind spot, the respective dataset is supplemented with the morphological data of the optic disc obtained by means of the OCT measurement. Also, the database can preferably contain datasets of a number of healthy eyes and also datasets of eyes with glaucoma in different stages. In this way, an improved differentiation and characterization of the functional data obtained with the analysis method is made possible. Also, the statistical connection between the functional data and the morphological data of one eye, respectively, can be derived from the datasets contained in the database. This connection can be determined with particular accuracy if the database contains a plurality of datasets of different eyes.

In order to obtain representative measuring results of the retinal nerve fiber layer, the optic disc or of an area of the optic disc to be determined, it may suffice to measure predetermined points, preferably at least six predetermined or pre-chosen points, of the retina. It has been found in particular that there are more or less strongly pronounced statistically significant relations between the measured points on the retina and areas of the eye's optic disc. For instance, some of the points of the retina and their measuring results can hardly give any clue to the morphological data of the optic disc, whereas other points have a close statistical relation to the morphological data of the optic disc. These points can thus preferably be used for deriving the morphological data of the optic disc so as to simplify the analysis method. For determining the morphological data of all areas of the optic disc, all points of the retina or of the field of vision can be utilized.

In particular, a selection of the predetermined points from the database can take place. Hence, the database can be used for locating the predetermined points in the first place.

A selection and a weighting of the predetermined points with regard to their relevance for determining the morphological data can take place. In that case, it can then be established, by means of a statistical calculating method, which of the predetermined points are especially suited for determining the morphological data. The points of the field of vision can then be weighted or prioritized differently so that the functional measuring results of the respective points have a different influence on the derived morphological data or so that only a specific number of the points of the retina are used at all for determining the morphological data. In doing so, a measuring result of the analysis method can be further improved.

The statistical relation between the functional measuring results of the points and the morphological data of the eye's optic disc can be mathematically established by means of regression analysis, preferably simple linear regression, multiple regression or stepwise multiple regression. This calculation can then be carried out for all datasets contained in the database so that, as a result, the statistically significant relation between the measuring results of the points and the defects of the eye's optic disc is obtained. The functional data of a patient's eye obtained by means of the analysis method or by a perimeter measurement can subsequently be determined as described before and then be derived according to the statistically significant relation with the help of the database.

In a special embodiment of the method it can be provided that the database contains only datasets of the predetermined points. This means that, in a first method step, first the datasets with functional and morphological data of eyes are collected and the points of the retina are determined that promise with high probability a measuring result approximate to the objective morphological data of the optic disc or which promise a significantly improved derivation or estimation of the morphological data of the optic disc. In this way it is possible in a second method step to perform the perimetric measurement of a patient's eye to be examined and to derive the morphological data of the optic disc of the eye alone from the predetermined points that were measured. Thus, the database only has to contain datasets of the predetermined points in the second method step. In this way, an extent of the database can be significantly reduced. In consequence, ophthalmological devices can then be used, for example, with which only the second step of the method is performed and which then would not have to contain all datasets that were used in the first method step.

A measuring result can be improved even further if, for example during the selection of the predetermined points and/or derivation of the morphological data, a person's age or a patient's and/or subject's age is taken into account. This is advantageous insofar as the influence of nerve fibers correlates to age. Potential age-related influences on the measuring results can thus be considered.

In another advantageous embodiment of the method, the measuring results of the measured points can be compared to the datasets for respectively corresponding points stored in the database, wherein then the morphological data of the optic disc of the eye are derived from the datasets of the eye that, in the comparison, have an approximate coincidence or high correlation with the measuring results of the measured points. In consequence, the respective measuring result of a point or a measured value of a point can be compared in every comparison to the stored measured values and then a morphological value associated with the stored measured value can be associated to the measured functional measured value. Depending on the coincidence or correlation of the measured functional data with the stored functional data, the stored morphological data can additionally be adjusted or corrected so that particularly accurate measuring results can be obtained.

In particular a discrepancy between the measuring results of the measured points and the measuring results stored in the database of the respectively corresponding points of the datasets can be utilized as a comparison criterion for the comparison. For example, a discrepancy of the measuring results of the measured points in comparison to the factual measuring results stored in the database in the respectively corresponding points of the retina allows a suitable selection of a morphological measured value or a corresponding correction of said measured value with the help of the discrepancy between the measuring results.

As morphological data, a nerve fiber layer thickness in an area of the optic disc and/or in a directly adjacent area of the optic disc can be determined. A measurement or determination of a nerve fiber layer thickness could be used particularly well for diagnosing glaucoma.

Also, the morphological data of a circular ring area (rim area) of the optic disc or a ratio of the circular ring area to an inner circle area (disc area) of the optic disc can be determined. The circular ring area is influenced in particular by the inner circle area, which substantially corresponds to a size of a blind spot. Nevertheless, it is possible to use the circular ring area and the inner circle area as respective morphological data in the course of the proposed method and to store them in the database. In this way, from a result of the measurement, also the circular ring area and the inner circle area or also a percentage value of a ratio of the circular ring area to the inner circle area can be produced.

In the course of the method, it is also advantageous if the optic disc and/or a retinal nerve fiber layer is divided into circle segments, wherein then the morphological data for each of the circle segments can be determined. For instance, the optical disc can be divided into 25 circle segments with a respective angular aperture of 14.4°. It has been found that a division into 25 circle segments is sufficient for obtaining measuring results with the proposed method which substantially correspond to the measuring results of an OCT measurement or come close thereto. In this way, it is also possible to determine a statistically significant relation between the measured points or considered points of the retina and the circle segments so as to use them for deriving the morphological data of the circle segments.

As a result of the measurement, a comparison of the measured functional data of a patient's optic disc can be stated in a ratio of at least one percentile rank of functional data of the optic disc of a representative control group of subjects. As a representative control group of subjects an average population can be chosen. The percentile rank of functional data can then be stated in percentile of the control group. Also, the result of the measurement can be stated and displayed by means of a comparison to several percentile ranks of functional data of the control group. A display can take place for example in the form of a graphic or tabular display on a screen of the ophthalmological device. In this way, a direct statement can be made as to how the currently measured eye or its morphological data is to be rated in comparison to the average population.

Also, it can be provided that a median and/or a standard error is determined and displayed for the derived morphological data of the optic disc. Then, it also becomes possible, for example, to assess the derived morphological data with regard to a probability of coincidence with the objective morphological data of the eye.

Further, the invention relates to an ophthalmological device, in particular a perimeter or the like, which is configured for the implementation of the method according to any of the preceding claims.

Advantageous embodiments of the ophthalmological device result from the dependent claims referring to the method claim.

BRIEF DESCRIPTION OF THE DRAWING FIGURES

In the following, the invention is explained in more detail with reference to the enclosed drawing.

FIG. 1 shows a schematic top view of an optic disc with surrounding nerve fiber areas;

FIG. 2 shows an enlarged illustration of the optic disc of FIG. 1;

FIG. 3 shows another schematic illustration of the optic disc with a measuring area;

FIG. 4 shows a schematic illustration of an ophthalmological device for the implementation of the analysis method;

FIG. 8 shows a diagram of a nerve fiber layer thickness, related to a circumference of an optic disc for different measurements;

FIG. 9 shows a diagram of a frequency distribution of a nerve fiber layer thickness related to the circumference of an optic disc in comparison to a first OCT measurement;

FIG. 10 shows the diagram of FIG. 9 in comparison to a second OCT measurement;

FIG. 14 shows the diagram of FIG. 9 in comparison to an OCT measurement in a patient with glaucoma;

FIG. 15 shows the diagram of FIG. 9 in comparison to a perimetric measurement in a patient with glaucoma with a low standard error;

FIG. 16 shows the diagram of FIG. 9 in comparison to a perimetric measurement in a patient with glaucoma with a high standard error;

FIG. 17 shows the diagram of FIG. 9 in comparison to a perimetric measurement in a patient with glaucoma with a range indication of a measuring result.

DETAILED DESCRIPTION

Figure 5:
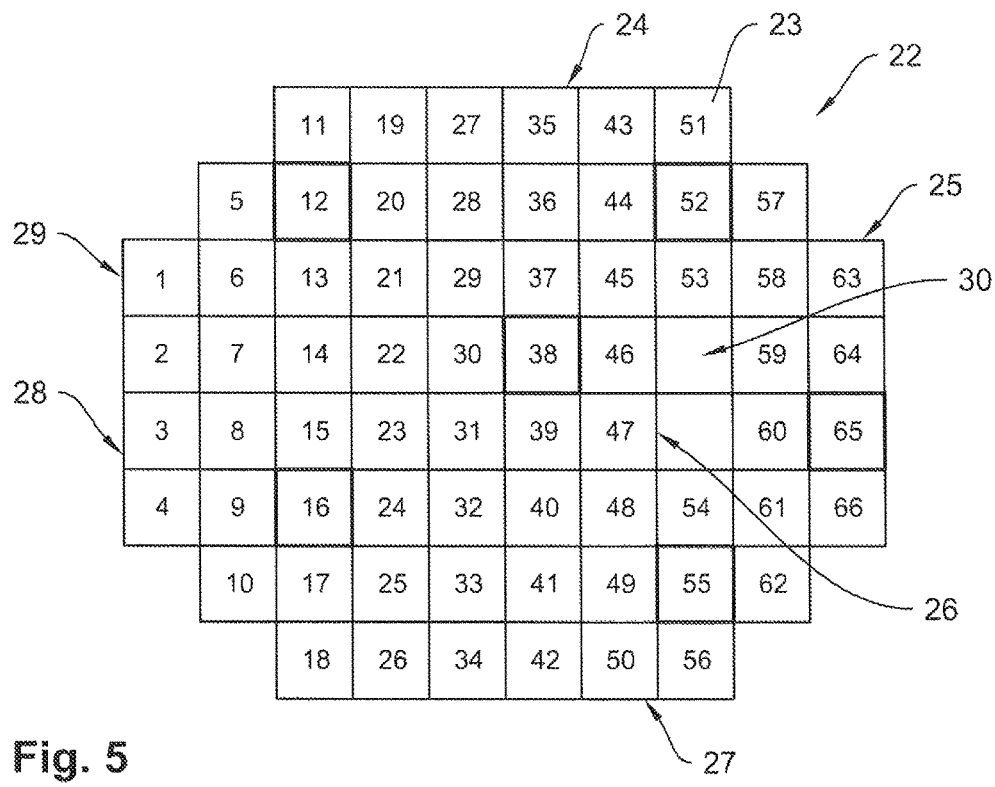
FIG. 5 shows a point matrix representing a field of vision.

FIG. 1 shows an optic disc 10 or optic nerve head (ONH) with schematically illustrated nerve fiber pathways 11, which extend in an arched manner from the optic disc 10 and which branch into individual photoreceptors, which are not illustrated in detail here and which form a retina 12. Thus, the nerve fiber pathways 11 leave a non-illustrated eye in bundles in the area of the optic disc 10 so that there are no photoreceptors in the area of the optic disc 10. Hence, the area of the optic disc 10 is also called the blind spot of the field of vision.

FIG. 2 shows a more detailed illustration of the optic disc 10, from which it becomes clear that the nerve fiber pathways 11 form an anatomical area called circular ring area 13 or also rim area (RA). The circular ring area 13 is particularly interesting in terms of an interpretation of possible damage to the optic disc 10 as a result of glaucoma. For an assessment, a percentage ratio of the circular ring area 13 to an inner circular area 14 of the optic disc 10 is typically employed as well.

Further, it is known to measure a nerve fiber layer thickness in the circumferential area 15 illustrated in FIG. 3, which is also called circular region (C), as an assessment criterion for glaucoma. The circumferential area 15 coaxially surrounds the optic disc 10, wherein a nerve fiber layer thickness along the circumference is typically not formed linear, but fluctuates or is non-uniform.

FIG. 4 shows a schematic illustration of an embodiment of a perimeter 16 configured for the implementation of the method. The perimeter 16 measures the field of vision of a person's eye, the perimeter 16 comprising means for data processing 17, a measuring device 18, a database 19, a display device 20 and a stimulation device 21. The means for data processing 17 are connected to the database 19, the display device 20 and the measuring device 18. For the measurement, the stimulation device 21 provides optical stimuli to the field of vision of a patient's or subject's eye, the patient affirming when he recognizes the stimuli. This is registered by the measuring device 18 and transmitted to the means for data processing 17, which derives morphological data of the optic disc of the eye according to the analysis method, taking into account datasets stored in the database 19, and displays said morphological data numerically and/or graphically by means of the display device 20.

With the help of FIGS. 4 to 7, a possible process of the analysis method will be exemplarily explained in the following. Further, from EP 2 361 547 A1, a method for obtaining functional data of a field of vision is known, which can be employed for acquiring functional data in the course of the proposed analysis method. Generally, however, any type of point matrix can be used for the implementation of the analysis method.

FIG. 5 shows a potential point matrix 22, which represents a measurable field of vision of an eye's retina not illustrated here. This means that, by the perimeter 16, an eye is exposed to stimuli in the form of light points of defined intensity in such a manner that a stimulus can be associated to one of the points 23 defined in the point matrix 22. The points 23 in the point matrix 22 are labeled with the numbers 1 through 66 for an improved differentiation. Where in the following there is reference made to one of the points 23, the format Pnn is used to designate said point.

The point matrix 22 is divided into six nerve fiber areas 24 to 29, which represent nerve fiber areas of a retina, which differ in terms of functionality. In particular, the nerve fiber pathways 11 or the areas of the retina formed by the nerve fiber pathways 11, respectively, correspond to the nerve fiber areas 24 to 29 of the field of vision. An area 30 of the point matrix 22 represents an optic disc 10 or blind spot of the field of view. In the course of the method described in EP 2 361 547 A1 for measuring the field of vision, the points 23 serve the determination of the field of vision and for obtaining the functional data, respectively.

Figure 7:
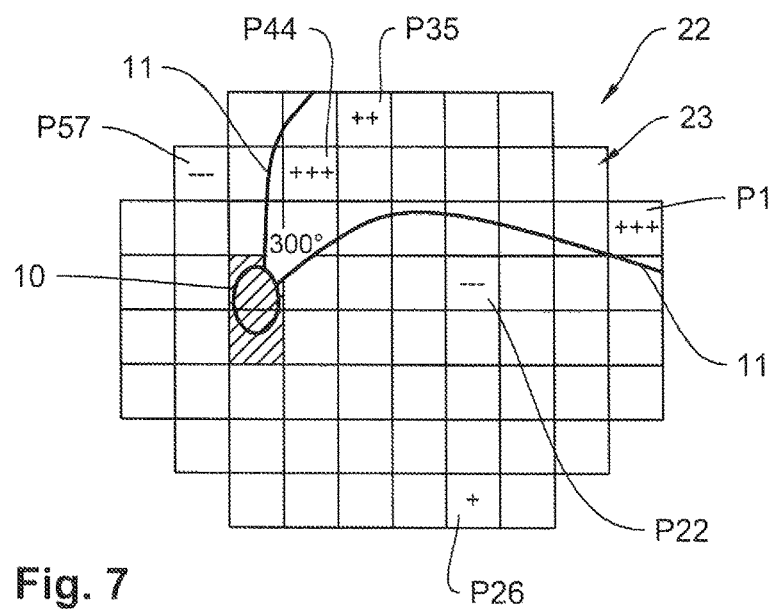
FIG. 7 shows the point matrix of FIG. 5 with predetermined points.
Figure 6:
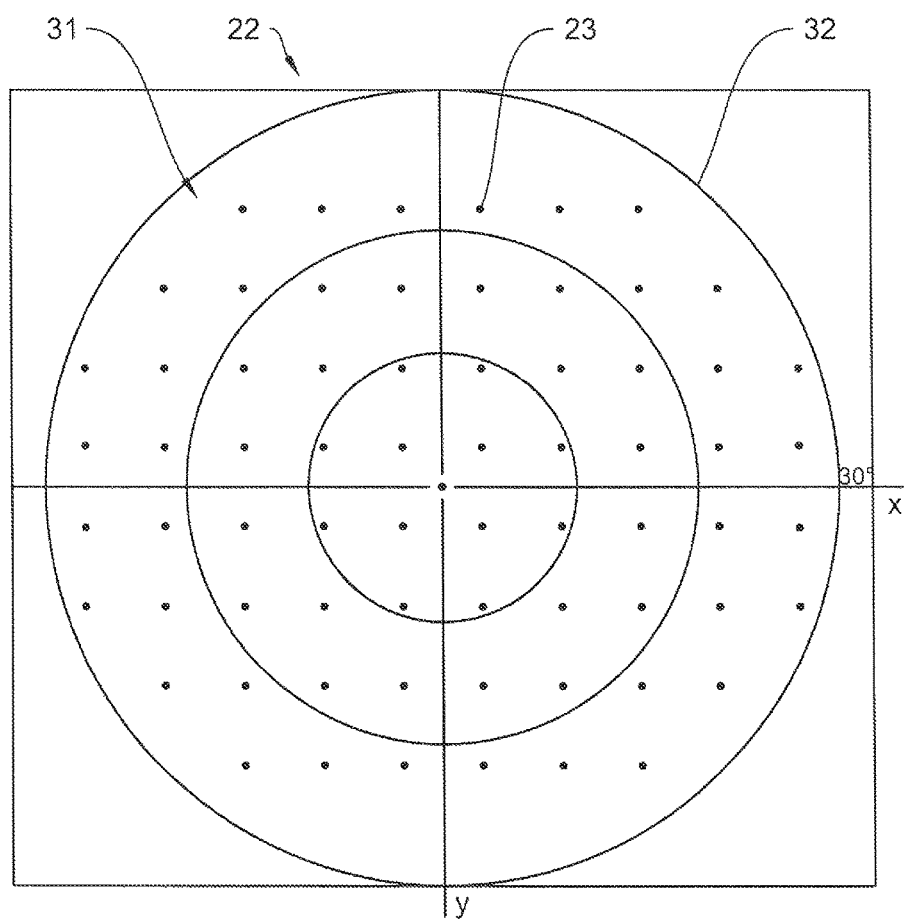
FIG. 6 shows a point matrix from a subject's or patient's point of view.

FIG. 6 shows an illustration of the point matrix 22 of the perimeter 16, not illustrated in detail, from a patient's or subject's point of view. A test area 31 is made up of 68 points 23, which form an orthogonal matrix within a 30° circle 32. A horizontal and a vertical distance between neighboring points 23 corresponds to 6°, respectively. The points 23 are arranged symmetrically relative to the axes X and Y, no points 23 lying directly on the axes X/Y. The maximal eccentricity of the points 23 is +/−27° in a horizontal direction and +/−21° in a vertical direction FIG. 7 shows the point matrix 22 in a mirror-inverted illustration with the points 23 and a supplementary illustration of the optic disc 10 with nerve fiber pathways 11. A position of 300° is mirrored horizontally and vertically with respect to the illustration in FIG. 3. From the number of points 23, six predetermined points P1, P22, P26, P35, P44 and P57 were determined, which have a statistically significant relation to morphological data of the optic disc 10. In correspondence to the relevance of the relation, the points 32 that have a direct connection to a nerve fiber layer thickness of the optic nerve 10 are labeled "+++" and "++". Further, the points 23 that have a negative connection to the nerve fiber layer thickness are labeled "−−−". Since also points 23 in a peripheral area of the field of vision have a statistically significant relation to the nerve fiber layer thickness, they are taken into account here as well and are labeled "+"

Thus, in the method, an asymmetry between the functional nerve fiber pathways 24 to 29 and the non-illustrated circle segments of the circumferential area 15 or the circular ring area 13 of the optic disc 10 is taken into account by including points 23 that are arranged at a distance to the optic disc 10. Thus, in the method, not only a loss of sensitivity of the nerve fiber areas 24 to 29 or points 23 is considered, but also a deviation from a homogenous distribution of the sensitivity in proximal and distal areas of the field of vision.

From the perimetric measurement of the field of vision and for determining the functional data of the predetermined points P1, P22, P26, P35, P44 and P57, the morphological data of the optic disc 10 are now derived. In principle, any suitable perimetric measuring method can be employed for determining the functional data of the points 23. The examples listed here to describe the method assume the fact that the perimetric examination was carried out with the method described in EP 2 361 547 A1. In said method, threshold values are measured in 66 points 23 of the field of vision and a nerve fiber layer thickness is calculated for each circle segment or sector of the circumferential area 15 of the optic disc 10 with the help of a linear formula which can contain threshold values of up to six measured points 23.

With regard to FIG. 7, a calculation of the nerve fiber layer thickness of a circle segment at 300° (of 360°) is exemplarily illustrated in the following. According to the method, six threshold values or points 23 are significant for a scale value of this circle segment or circle angle of the optic disc 10. The coefficients of the linear formula are taken from the database 19. The database 19 contains datasets with functional data of a field of vision and with morphological data of an optic disc 10 of a representative control group of the population. The coefficients result from a statistically significant connection, determined by linear regression, between the functional and the morphological data. The threshold values multiplied with the points 23 are indicated in decibel, respectively.

$$D(300)=86{,}58+3.21*P(1)-3.59*P(22)+0.96*P(26)+2.08*P(35)+3.67*P(44)-4.60P*(57)$$

Aside from the patient's or subject's age in years, eleven other threshold values or points 23, which are significant here, are used for calculating the percentage ratio of the circular ring area 13 to the inner circle area 14 in a similar manner. The formula in this case is as follows:

$$RA(\%)=0.37*A+2.41*P(5)-1.48*P(13)+1.97*P(26)-1.33*P(30)-1.26*P(30)-1.26*P(31)-0.85*P(35)+2.66P(37)+1.08*P(54)+1.99*P(56)-1.37*P(63)$$

FIG. 8 shows a diagram with an indication of a nerve fiber layer thickness in micrometers on an abscissa and with an indication of pixels on an ordinate, the value range to the ordinate here corresponding to the circumferential area 15 of 360°. The circumferential area 15 starts in the temporal area of the optic disc (position zero) and runs through the superior, nasal and inferior areas back to the temporal area (position 256), analogically to an illustration of an OCT measurement. The continuous line in FIG. 8 shows the measuring result of an OCT measurement. The dashed line shows a mean value of a measurement carried out by means of the proposed perimetric method. The dotted line shows the mean value taking into account larger deviations of the measured value.

FIG. 9 shows a diagram illustration corresponding to the diagram in FIG. 8 with an indication of percentile ranks for a normal population as the control group. Between the lines 33 and 34, a range between 5 and 95 percentile of the control group is illustrated. Between the line 34 and a line 35, a range of 1 to 5 percentile of the control group is illustrated. Below line 35, a range of below 1 percentile of the control group is illustrated. A line 36 indicates the result of a first OCT measurement in a patient.

FIG. 10 shows the diagram of FIG. 9 with the difference of a second OCT measurement in the patient.

Figure 11:
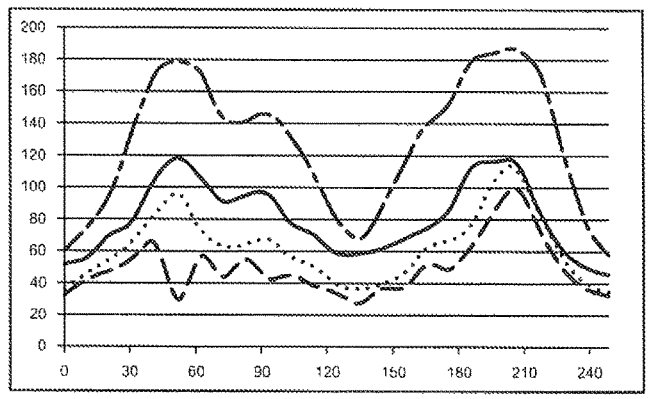
FIG. 11 shows the diagram of FIG. 9 in comparison to a perimetric measurement with a low standard error.
Figure 12:
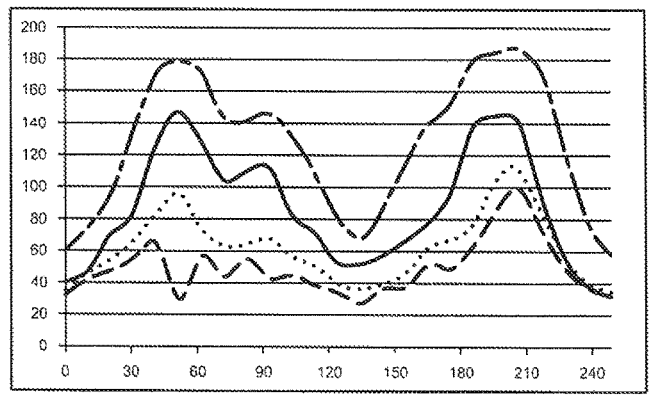
FIG. 12 shows the diagram of FIG. 9 in comparison to a perimetric measurement with a high standard error.
Figure 13:
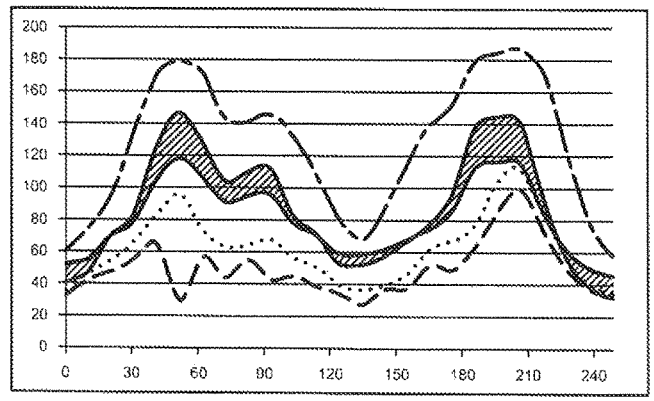
FIG. 13 shows the diagram of FIG. 9 in comparison to a perimetric measurement with a result range.

FIGS. 11 to 13 each show the diagram illustration of FIG. 9 with the illustration of the measured values of the control group, wherein, in FIG. 11 a measuring result, determined using the perimetric method, with a low standard error and, in FIG. 12, a measuring result with a high standard error is illustrated. FIG. 13 complementarily shows a range between the measuring result with high and low standard errors. Thus, in the exemplarily performed measurement in a healthy patient, a real, objective measuring result of a nerve fiber layer thickness will lie with high probability within the indicated range.

FIGS. 14 to 17 also each show diagram illustrations corresponding to the diagrams of FIG. 9 with respectively different illustrated measuring results relative to the illustrated control group. FIG. 14 shows a measuring result of an OCT measurement of an eye in a patient with diagnosed glaucoma.

FIG. 15 shows a measuring value of said patient, determined by means of the perimetric method, with a low standard error, FIG. 16 with a high standard error and FIG. 17 with an illustration of a range between the high and low standard error. It can be taken from the respective figures that the morphological data and measuring results determined using the perimetric method can be substantially compared to the measuring results of an OCT measurement.

The invention claimed is:

1. An analysis method for determining a morphological property of a retinal nerve fiber layer of an eye, whereby the analysis method is performed by means of a perimeter (16), and also means for data processing (17) using a database (19), the database comprises a plurality of datasets of healthy eyes and datasets of eyes with glaucoma, each of the datasets comprises functional data of a field of vision obtained by perimetric measurements and morphological data of a retinal nerve fiber layer obtained by OCT measurements, wherein, by means of the perimeter, functional data of a field of vision of the eye are measured, a retina of the eye being divided into points (23), which represent the field of vision, optical stimuli of a defined intensity being provided to predetermined points (P1, P22, P26, P35, P44, P57) of the retina which are selected from the database, a reaction to a stimulus being determined as a measuring result of a predetermined point, the measuring results of the predetermined points having a statistically significant relation to morphological data of a retinal nerve fiber layer of the eye, the morphological data of the retinal nerve fiber layer of the eye being derived from the measuring results of the predetermined points and from the datasets.

2. The method according to claim 1, characterized in that the morphological property of the retinal nerve fiber layer and an optic disk (10) of an eye is determined, whereby the datasets comprises morphological data of the retinal nerve fiber layer and the optic disk obtained by OCT measurements, the measuring results of the predetermined points (P1, P22, P26, P35, P44, P57) having a statistically significant relation to morphological data of the retinal nerve fiber layer and the optic disk of the eye, the morphological data of the retinal nerve fiber layer and the optic disk of the eye being derived from the measuring results of the predetermined points and from the datasets.

3. The method according to claim 1, characterized in that at least six predetermined points (P1, P22, P26, P35, P44, P57) are measured.

4. The method according to claim 3, characterized in that the selection and a weighting of the predetermined points (P1, P22, P26, P35, P44, P57) with regard to their ability for the determination of the morphological data takes place.

5. The method according to claim 1, characterized in that the statistical relation is determined by means of regression analysis, preferably a simple linear regression, multiple regression or stepwise multiple regression.

6. The method according to claim 1, characterized in that an age of a person is taken into account.

7. The method according to claim 1, characterized in that the measuring results of the measured points (23) are compared to the datasets stored in the database (19) for respectively corresponding points (P1, P22, P26, P35, P44, P57), the morphological data of a retinal nerve fiber layer of the eye being derived from the datasets, which in the comparison present an approximate coincidence or a high correlation with the measuring results of the measured points.

8. The method according to claim 7, characterized in that for the comparison, a discrepancy between measuring results of the measured points (23) and measuring results stored in the database of the respectively corresponding points (P1, P22, P26, P35, P44, P57) of the datasets is used as a comparison criterion.

9. The method according to claim 1, characterized in that as morphological data, a nerve fiber layer thickness in an area of a retinal nerve fiber layer is determined.

10. The method according to claim 1, characterized in that as morphological data, the retinal nerve fiber layer and a circular ring area (13) of an optic disc (10) or a ratio of the circular optic disk ring area and an inner circle area (14) of the optic disc is determined.

11. The method according to claim 1, characterized in that the retinal nerve fiber layer is divided into circle segments, the morphological data for each of the circle segments being determined.

12. The method according to claim 1, characterized in that as a result of the measurement, a comparison of the measured functional data of the retinal nerve fiber layer in a ratio to at least one percentile rank of functional data of the retinal nerve fiber layer of a representative control group of subjects is given.

13. The method according to claim 1, characterized in that a median and/or a standard error is determined for the derived morphological data of the retinal nerve fiber layer.

14. A perimeter (16), comprising means for data processing (17), a measuring device (18), a database (19), a display device (20) and a stimulation device (21), configured for the implementation the method according to claim 1.

15. The method of claim 1, wherein the morphological data of the retinal nerve fiber layer comprises a nerve fiber layer thickness.

16. An analysis method for determining a morphological property of an optic disc of an eye, whereby the analysis method is performed by means of a perimeter (16), and also means for data processing (17) using a database (19), the database comprises a plurality of datasets of healthy eyes and datasets of eyes with glaucoma, each of the datasets comprises functional data of a field of vision obtained by perimetric measurements and morphological data of an optic disc obtained by OCT measurements, wherein, by means of the perimeter, functional data of a field of vision of the eye are measured, a retina of the eye being divided into points (23), which represent the field of vision, optical stimuli of a defined intensity being provided to predetermined points (P1, P22, P26, P35, P44, P57) of the retina which are selected from the database, a reaction to a stimulus being determined as a measuring result of a predetermined point, the measuring results of the predetermined points having a statistically significant relation to morphological data of an optic disc of the eye, the morphological data of the optic disc of the eye being derived from the measuring results of the predetermined points and from the datasets.

17. The method of claim 16, wherein the morphological data of the optic disc comprises a circular ring area.

* * * * *